(12) United States Patent
Lakshmanan et al.

(10) Patent No.: US 11,890,223 B2
(45) Date of Patent: Feb. 6, 2024

(54) HEATING AND COOLING DEVICE

(71) Applicant: THE REGENTS OF THE UNIVERSITY OF MICHIGAN, Ann Arbor, MI (US)

(72) Inventors: Sridhar Lakshmanan, Belleville, MI (US); Michael William Putty, Grosse Pointe Woods, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 113 days.

(21) Appl. No.: 16/604,033

(22) PCT Filed: Apr. 24, 2018

(86) PCT No.: PCT/US2018/029073
§ 371 (c)(1),
(2) Date: Oct. 9, 2019

(87) PCT Pub. No.: WO2018/200474
PCT Pub. Date: Nov. 1, 2018

(65) Prior Publication Data
US 2021/0100682 A1 Apr. 8, 2021

Related U.S. Application Data

(60) Provisional application No. 62/489,138, filed on Apr. 24, 2017.

(51) Int. Cl.
*A61F 7/00* (2006.01)
*A61F 7/02* (2006.01)

(52) U.S. Cl.
CPC ...... *A61F 7/007* (2013.01); *A61F 2007/0075* (2013.01); *A61F 2007/0079* (2013.01);
(Continued)

(58) Field of Classification Search
CPC .... A61F 7/007; A61F 7/03; A61F 2007/0075; A61F 2007/0077; A61F 2007/0079;
(Continued)

(56) References Cited

U.S. PATENT DOCUMENTS 5,969,290 A * 10/1999 Kagawa ................. H01L 35/08
136/201
2003/0097845 A1 5/2003 Saunders et al.
(Continued)

FOREIGN PATENT DOCUMENTS

EP 0827215 A2 3/1998

OTHER PUBLICATIONS

International Search Report and Written Opinion of the International Searching Authority issued in PCT/US2018/029073, dated Aug. 7, 2018; ISA/KR.
(Continued)

*Primary Examiner* — Kaitlyn E Smith
*Assistant Examiner* — Bradford C. Blaise
(74) *Attorney, Agent, or Firm* — Harness, Dickey & Pierce, P.L.C.

(57) ABSTRACT

A heating and/or cooling device for contact with a human body is provided having a power source outputting electrical energy, a temperature controller operably coupled to the power source configured to maintain a predetermined temperature parameter, and at least one heating and/or cooling module operably coupled to the temperature controller for selectively receiving the electrical energy and being responsive thereto to heat and/or cool the human body. The at least one heating and/or cooling module having a pair of electrodes spaced apart by a thermoelectric powder and an insulator at least partially surrounding the thermoelectric powder.

16 Claims, 10 Drawing Sheets

(52) U.S. Cl.
 CPC .............. *A61F 2007/0086* (2013.01); *A61F 2007/0233* (2013.01); *A61F 2007/0263* (2013.01); *A61F 2007/0295* (2013.01)

(58) Field of Classification Search
 CPC ...... A61F 2007/0086; A61F 2007/0088; A61F 2007/0093; A61F 2007/0233; A61F 2007/0263; A61F 2007/0295
 See application file for complete search history.

(56) References Cited

U.S. PATENT DOCUMENTS

| | | |
|---|---|---|
| 2005/0193742 A1 | 9/2005 | Arnold |
| 2007/0084497 A1 | 4/2007 | Strnad |
| 2008/0087314 A1 | 4/2008 | Xiao et al. |
| 2011/0284804 A1* | 11/2011 | Kim .......................... B22F 9/04 |
| | | 252/502 |
| 2014/0246065 A1 | 9/2014 | Lee |
| 2016/0374411 A1* | 12/2016 | Brooks ................... A61F 7/007 |
| | | 165/104.21 |
| 2017/0042479 A1* | 2/2017 | Shimuta ............... A61B 5/6804 |
| 2017/0224526 A1* | 8/2017 | Dufour ................... A61F 7/007 |

OTHER PUBLICATIONS

"Smart Shirt Monitors Key Vital Signs", Design Medical Briefs Insider, Apr. 3, 2017.

\* cited by examiner

HEATING AND COOLING DEVICE

CROSS-REFERENCE TO RELATED APPLICATIONS

This application is the U.S. National Phase Application under 35 U.S.C. 371 of International Application No. PCT/US2018/029073 filed on Apr. 24, 2018, which claims the benefit of U.S. Provisional Application No. 62/489,138, filed on Apr. 24, 2017. The entire disclosures of the above applications are incorporated herein by reference.

FIELD

The present disclosure relates to a heating and cooling device and, more particularly, relates to a heating and/or cooling device having a plurality of modules that can be worn and incorporated into materials for contact with the human body.

BACKGROUND AND SUMMARY

This section provides background information related to the present disclosure which is not necessarily prior art. This section also provides a general summary of the disclosure, and is not a comprehensive disclosure of its full scope or all of its features.

According to the principles of the present teachings, a heating and cooling device is provided that can cool and/or warm a human body. In some embodiments, the device includes a packaging of thermoelectric material that can either absorb heat (body cooling) or dissipate heat (body warming). In some embodiments, an inter-connection of a plurality of thermoelectric packages can be used to cover appropriate portions of the human body. In some embodiments, the plurality of thermoelectric packages can be configured in a network that enables the device to function as intended even if one or more connections fail. Still further, in some embodiments, the device that can be integrated into wearable garments using CNC Knitting Machines. It is envisioned that the device can be powered by a direct current (DC) or alternating current (AC) power source, and the power source may be integrated into wearable garments. A current or voltage regulator can control the absolute cooling and/or warming temperature and, in some embodiments, a current or voltage regulator can also control the rate of cooling and/or warming.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms, such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As introduced above, according to the principles of the present teachings, a wearable heating and/or cooling device is provided that can cool and/or warm the human body's temperature having advantageous construction and method of operation. In some embodiments, the device includes a packaging of thermoelectric material that can either absorb heat (body cooling) or dissipate heat (body warming). In some embodiments, an inter-connection of a plurality of thermoelectric packages can be used to cover appropriate portions of the human body. In some embodiments, the plurality of thermoelectric packages can be configured in a network that enables the device to function as intended even if one or more connections fail. Still further, in some embodiments, the device that can be integrated into wearable garments using CNC Knitting Machines. It is envisioned that the device can be powered by a direct current (DC) or alternating current (AC) power source, and the power source may be integrated into wearable garments. A current or voltage regulator can control the absolute cooling and/or warming temperature and, in some embodiments, a current or voltage regulator can also control the rate of cooling and/or warming.

According to the principles of the present teachings, as illustrated in FIGS. 1A-7B, a heating and/or cooling device 10 is provided according to any one of a number of embodiments. In some embodiments, heating and/or cooling device 10 can comprise one or more individual heating and/or cooling modules 11 operably coupled with a power source 50 and a temperature controller 52 via lines 54. As will be described herein, heating and/or cooling device 10 can be coupled to a single heating and/or cooling module 11 or can comprise a plurality of heating and/or cooling modules 11 arranged as an array 1000 (see FIGS. 3-7B). Array 1000 can be discretely configured to permit operation of each individual module 11 even if one or more modules 11 fail.

Figure 1A:
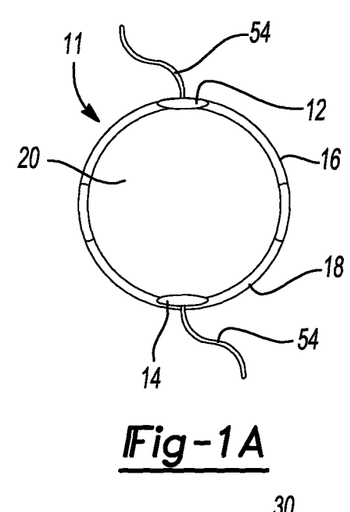
FIGS. 1A-1B illustrate a heating and/or cooling device according to the principles of the present teachings in a cylindrical thermoelectric package.
Figure 1B:
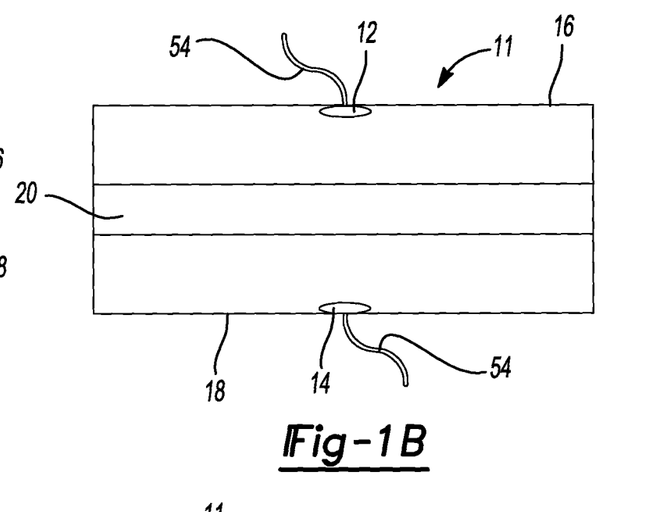
Figure 2A:
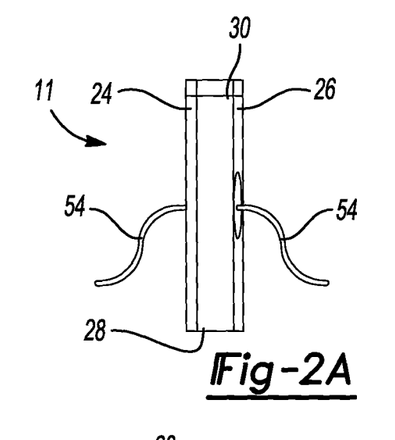
FIGS. 2A-2D illustrate a heating and/or cooling device according to the principles of the present teachings in a planar thermoelectric package.
Figure 2B:
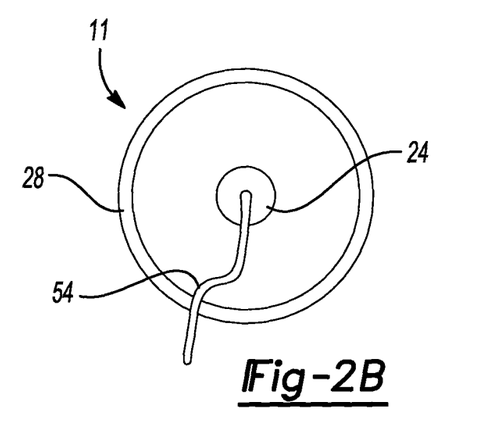
Figure 2C:
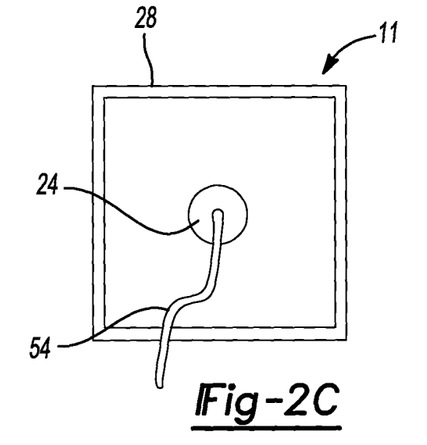
Figure 2D:
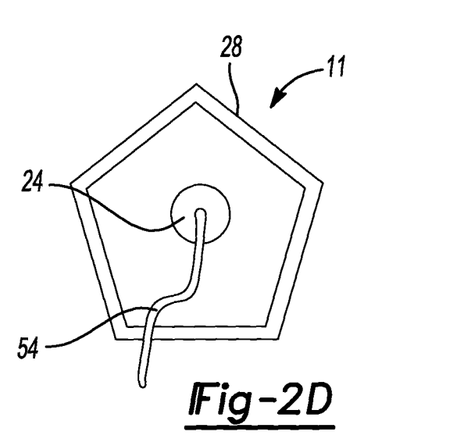

As illustrated in FIGS. 1A and 1B, the heating and/or cooling modules 11 can define a cylindrical shape having top and bottom curved electrode walls 12, 14 made out of electrode material, such as copper, graphite, titanium, brass, silver, or platinum. First and second insulator walls 16, 18 can be made of an insulator, such as fabric, foam, glass, plastic, rubber (e.g. silicon rubber), or wood. The same insulator 16, 18 also isolates the top electrode 12 from the bottom electrode 14. The insulator 16, 18 is able to protect the fillings of the cylinder from the environment, such as sweat, impact, detergent, fabric softener, or external heat, but remains thermally conductive and electrically insulating.

Silicon rubber is particularly useful, although alternatives may be used, and has the characteristic of being both an inorganic and organic material that provides good chemical stability and flame retardancy. Silicon rubber can be immersed in water for long periods of time with water absorption of about 1% and no effect on the mechanical strength. Under ordinary pressure, contact with steam causes almost no deterioration of silicon rubber and it further exhibits outstanding resistance to oil, solvents, and other chemicals at high temperature. Silicon rubber has high insulation resistance of 1 T ohm-m-1000 T ohm-m and its insulating properties are stable over wide range of temperature and across a wide frequency spectrum. The thermal conductivity of silicon rubber is about 0.2 W/(m.ohm.K), a value higher that of common organic rubbers. Some silicon rubber contain a high proportion of special inorganic filters to improve thermal conductivity (about 1.3 W/(m.ohm.K)).

Fillings 20 of the cylinder can be made of powdered thermoelectric material, such as Silicon-Germanium (SiGe), Lead Telluride (PbTe), Bismuth Telluride (Bi2Te3), Silver Antimony Telluride (AgSbTe2), Germanium Telluride (GeTe), Skutterudites (CoSb3), or Zinc Antimony (Zn4Sb3). Powdered material can be synthesized nano structures to, for example, enhance the thermoelectric properties of the material, including single walled carbon nanotubes (SWCNTs). Powdered material can be deposited or printed on the inner walls of the cylinder. In some embodiments, the total package size varies from 1 centimeter to several inches.

According to some embodiments, heating and/or cooling modules 11 can comprise a flat or generally planar shape, as illustrated in FIG. 2A-2D, that comprises front and back flat electrode walls 24, 26 made out of electrode material, such as copper, graphite, titanium, brass, silver, or platinum. Fully surrounding insulator walls 28, which can extend about a perimeter or periphery, are made out of an insulator, such as fabric, foam, glass, plastic, rubber (e.g. silicon rubber), or wood. The same insulator also isolates the front electrode 24 from the back electrode 26. The insulator 28 is also able to protect the contents of the flat shape from the environment, such as sweat, impact, detergent, fabric softener, or external heat. Content or filling 30 of the module 11 can be made of compacted/baked thermoelectric material, such as Silicon-Germanium (SiGe), Lead Telluride (PbTe), Bismuth Telluride (Bi2Te3), Silver Antimony Telluride (AgSbTe2), Germanium Telluride (GeTe), Skutterudites (CoSb3), or Zinc Antimony (Zn4Sb3). Baked material can be synthesized nano structures to, for example, enhance the thermoelectric properties of the material. In some embodiments, the total package size varies from 1 centimeter to several inches.

In some embodiments, wearable heating and/or cooling device 10 comprises one or more individual heating and/or cooling modules 11 being interconnected using electrical wiring 54, as illustrated in FIGS. 1A-1B, 2A-2D, and 3. Wiring 54 is made of materials, such as Copper or Aluminum. The wiring 54 is soldered onto the electrodes 12, 14,

24, 26 of the wearable heating and/or cooling device. For example, solder alloys of Tin-Lead, Tin-Zinc, Lead-Silver, Zinc-Aluminum, Tin-Silver, or Tin-Bismuth can be used. The number of individual wearable heating and/or cooling modules 11 coupled together into an array or other arrangement depends on the area of the human body that is to be cooled or warmed. The total package size varies from a few centimeters to several feet.

Figure 3:
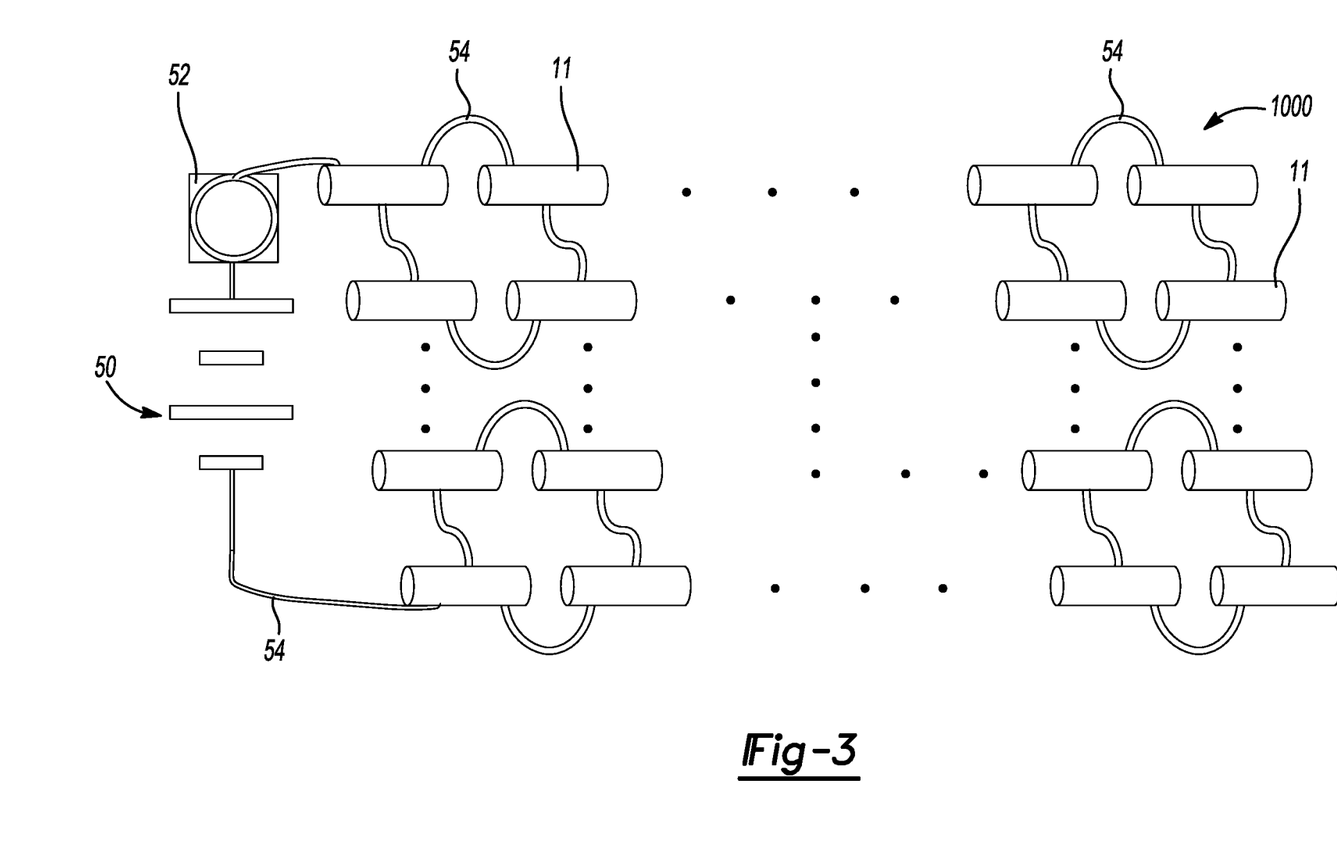
FIG. 3 illustrates a heating and/or cooling device according to the principles of the present teachings having an array of heating and/or cooling modules.
Figure 4A:
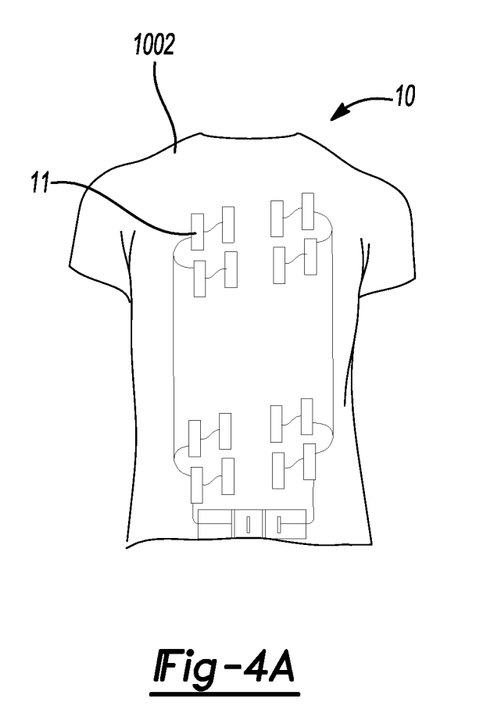
FIGS. 4A-4I illustrate the heating and/or cooling device according to the principles of the present teachings incorporated in a plurality of wearable products.
Figure 4B:
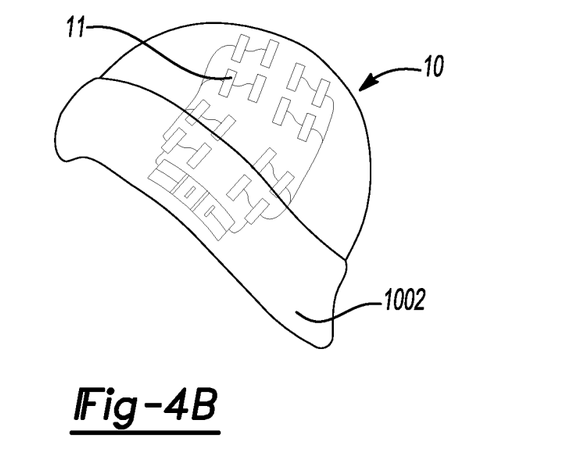
Figure 4C:
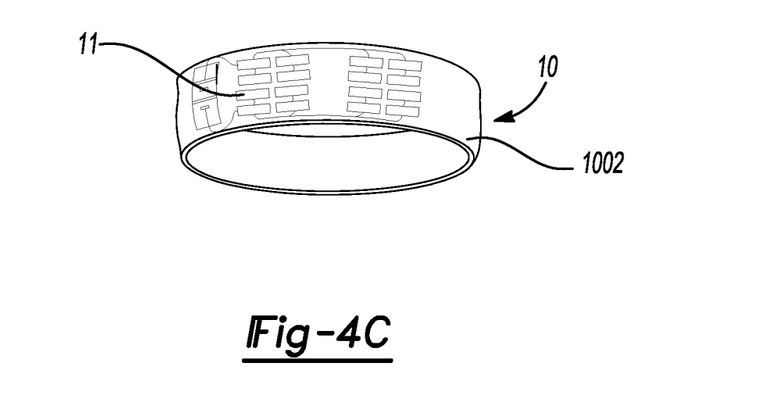
Figure 4D:
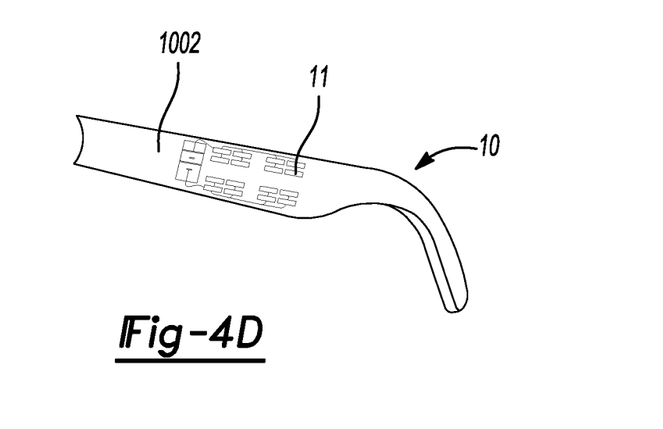
Figure 4E:
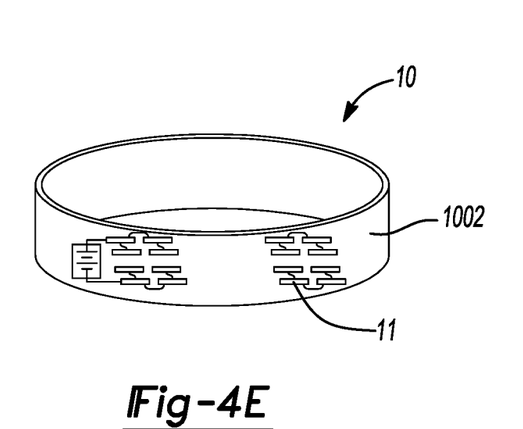
Figure 4F:
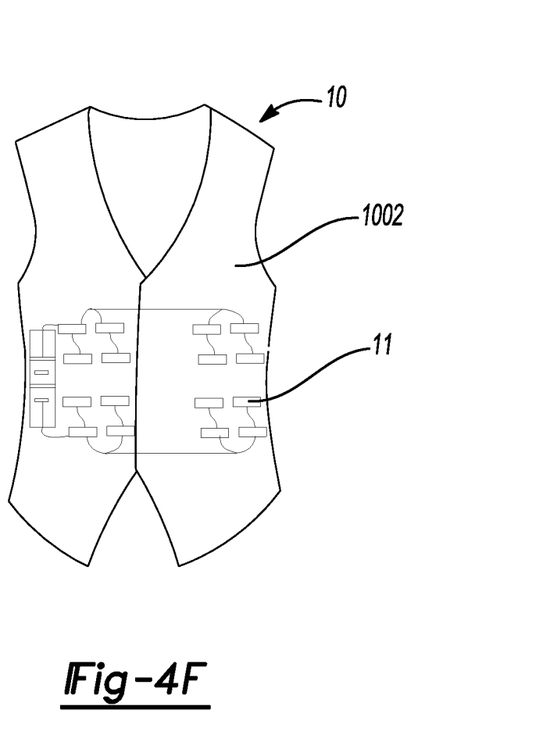
Figure 4G:
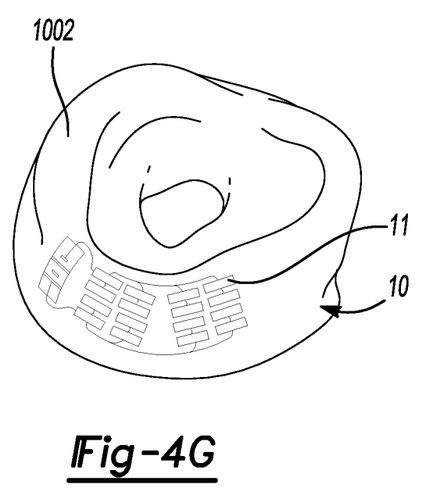
Figure 4H:
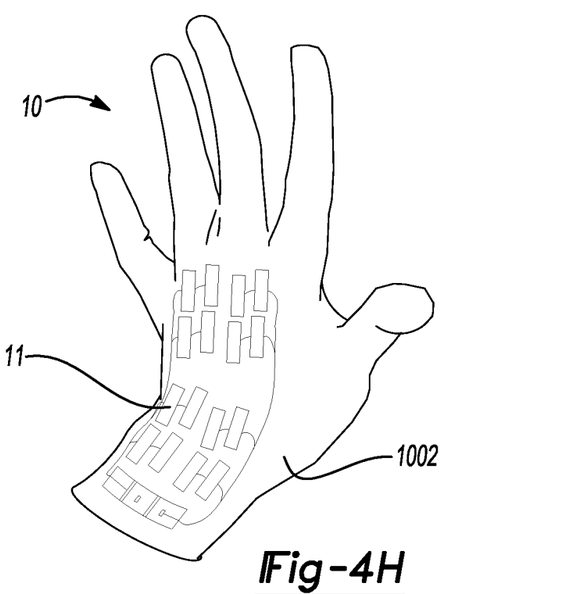
Figure 4I:
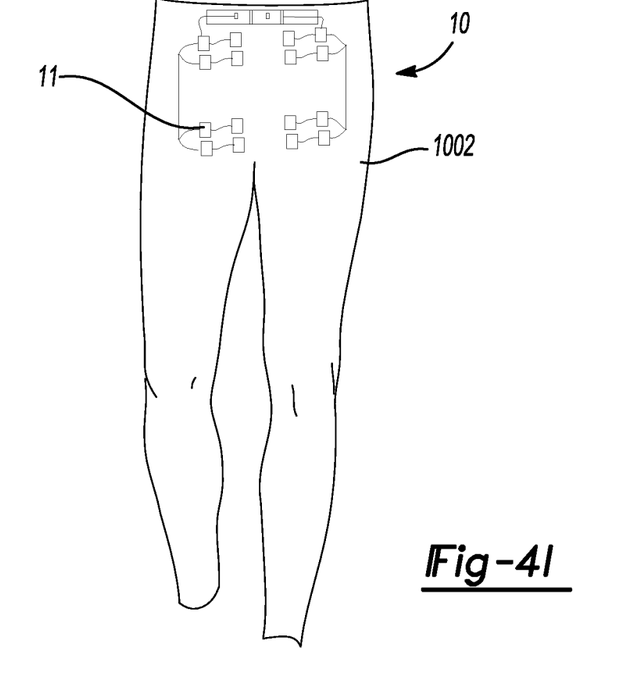
Figure 5A:
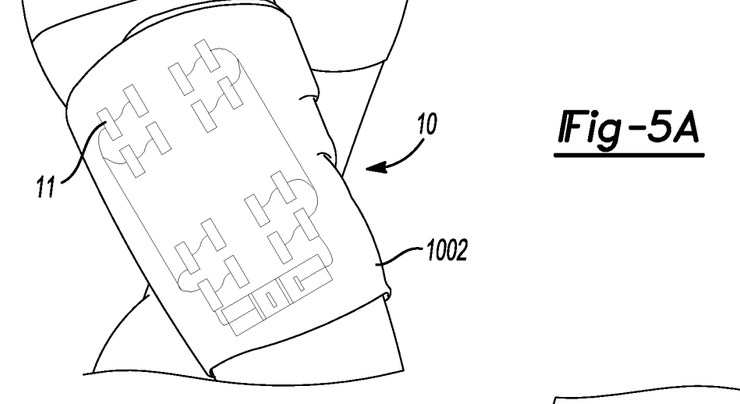
FIGS. 5A-5F illustrate the heating and/or cooling device according to the principles of the present teachings incorporated in a plurality of athletic support products.
Figures 5B, 5C:
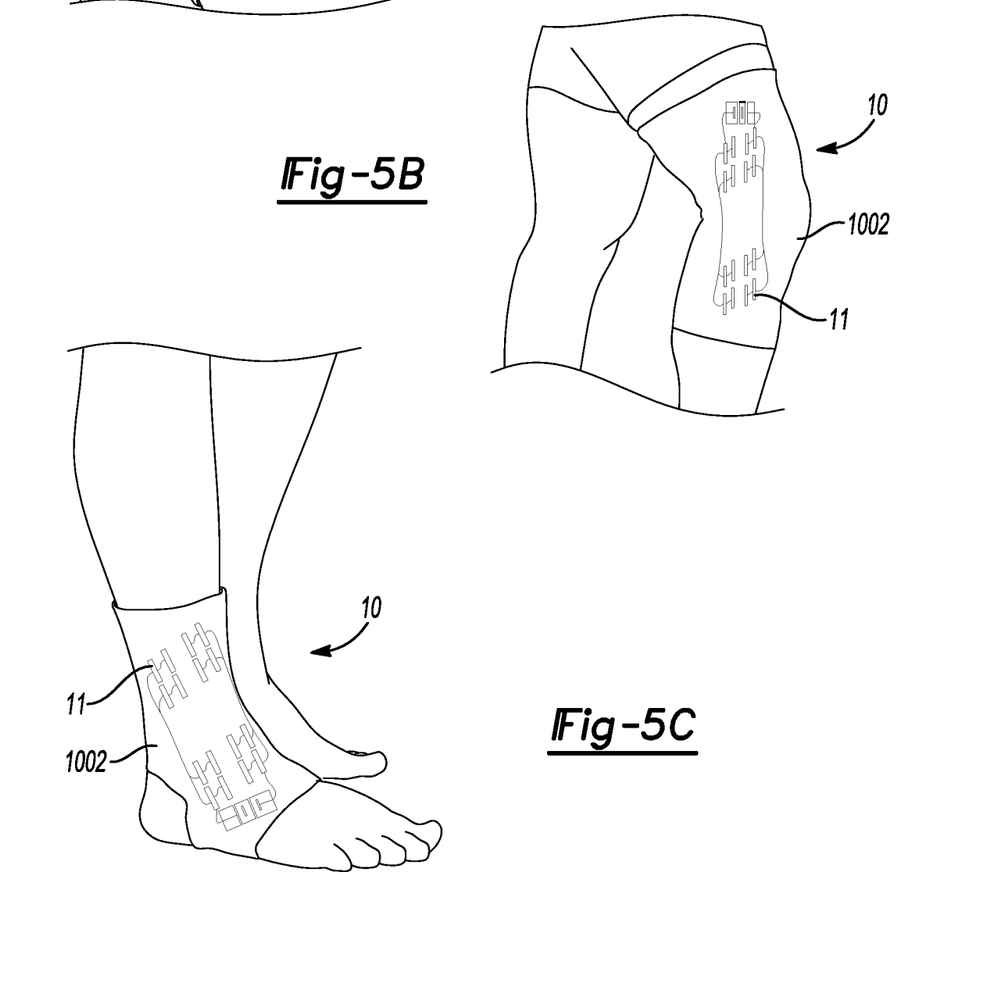
Figures 5D, 5E:
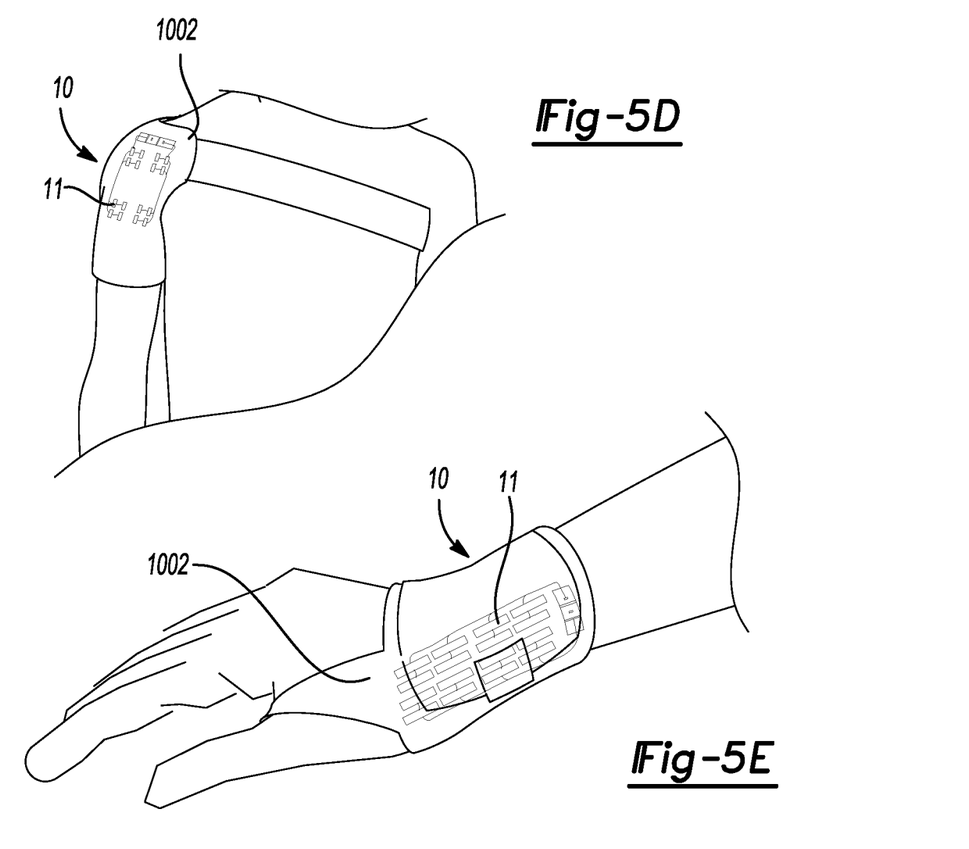
Figure 5F:
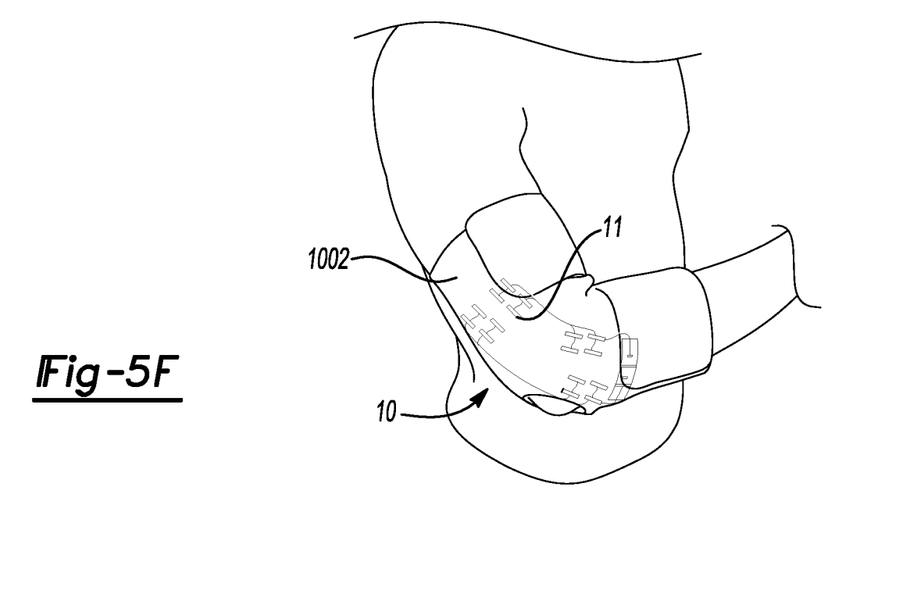
Figures 6A, 6B, 6C:
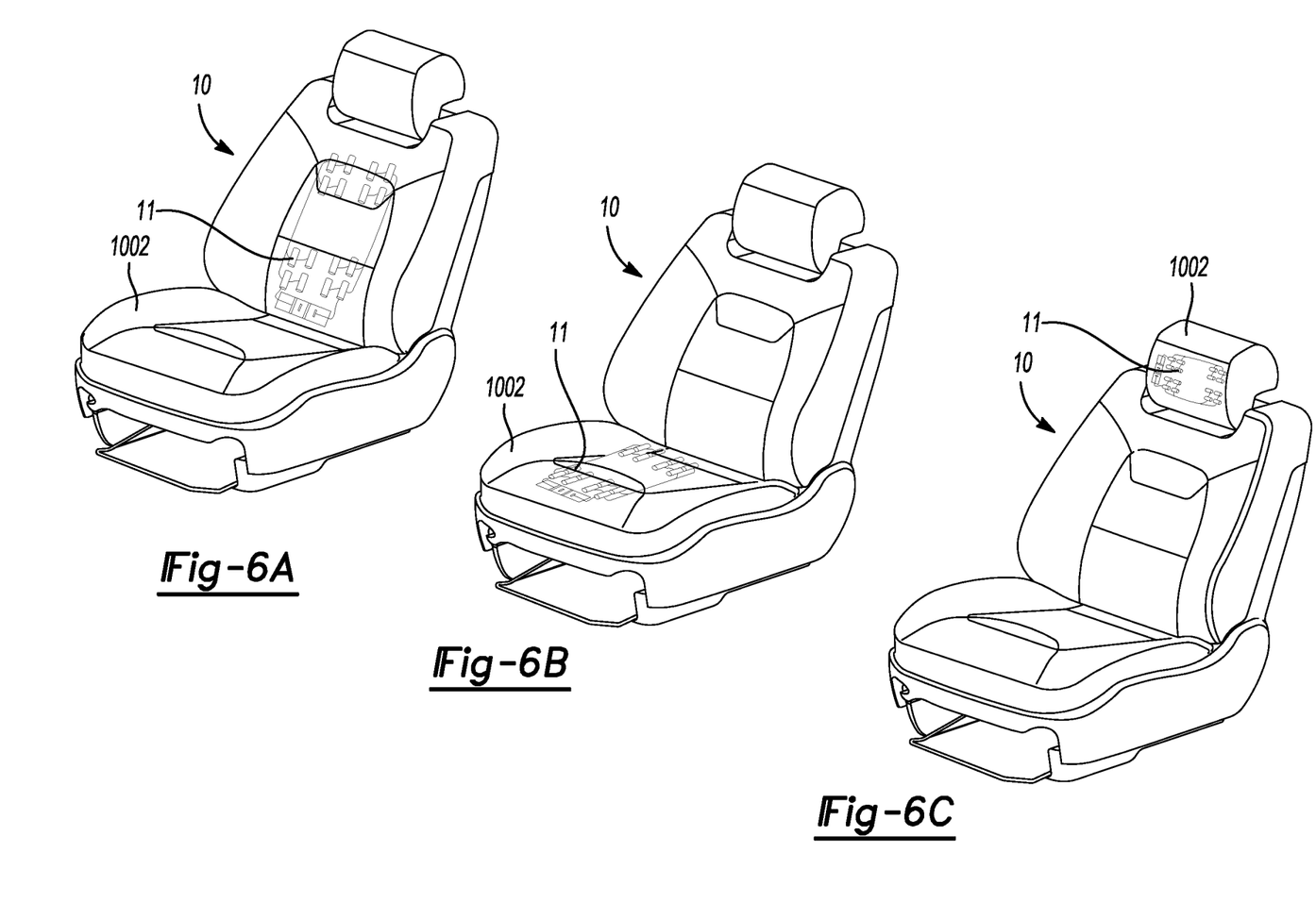
FIGS. 6A-6D illustrate the heating and/or cooling device according to the principles of the present teachings incorporated in a plurality of seating device located in the back support area, seat area, head area, and armrest area, respectively.
Figure 6D:
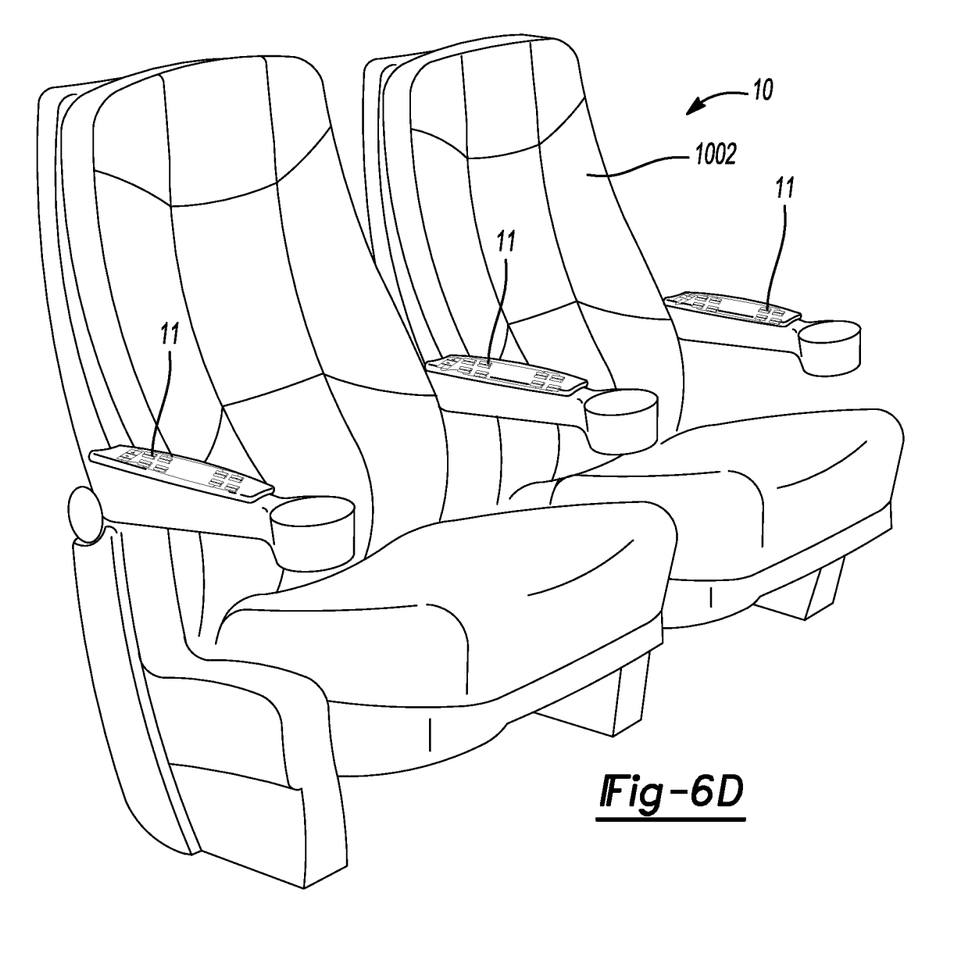
Figure 7A:
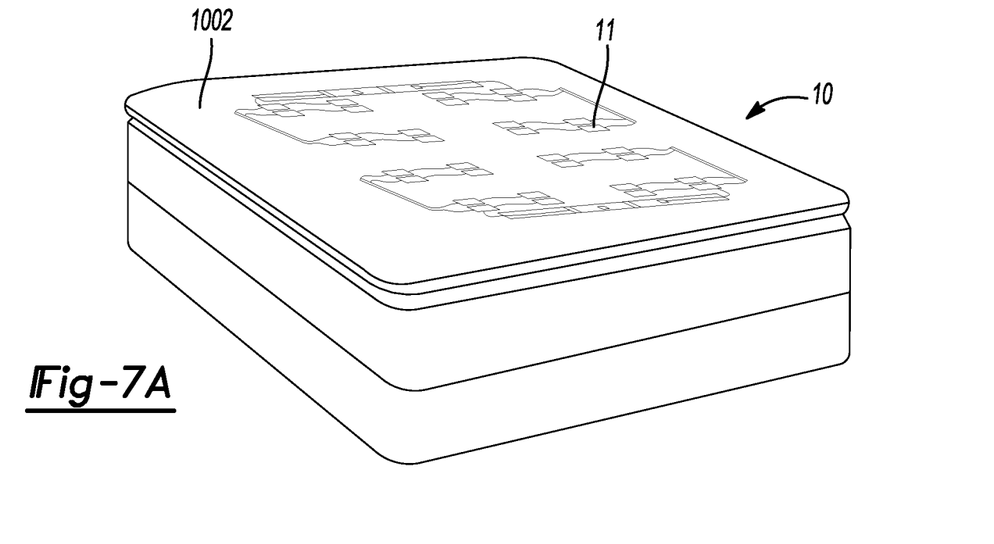
FIG. 7A illustrate the heating and/or cooling device according to the principles of the present teachings incorporated in a mattress.
Figure 7B:
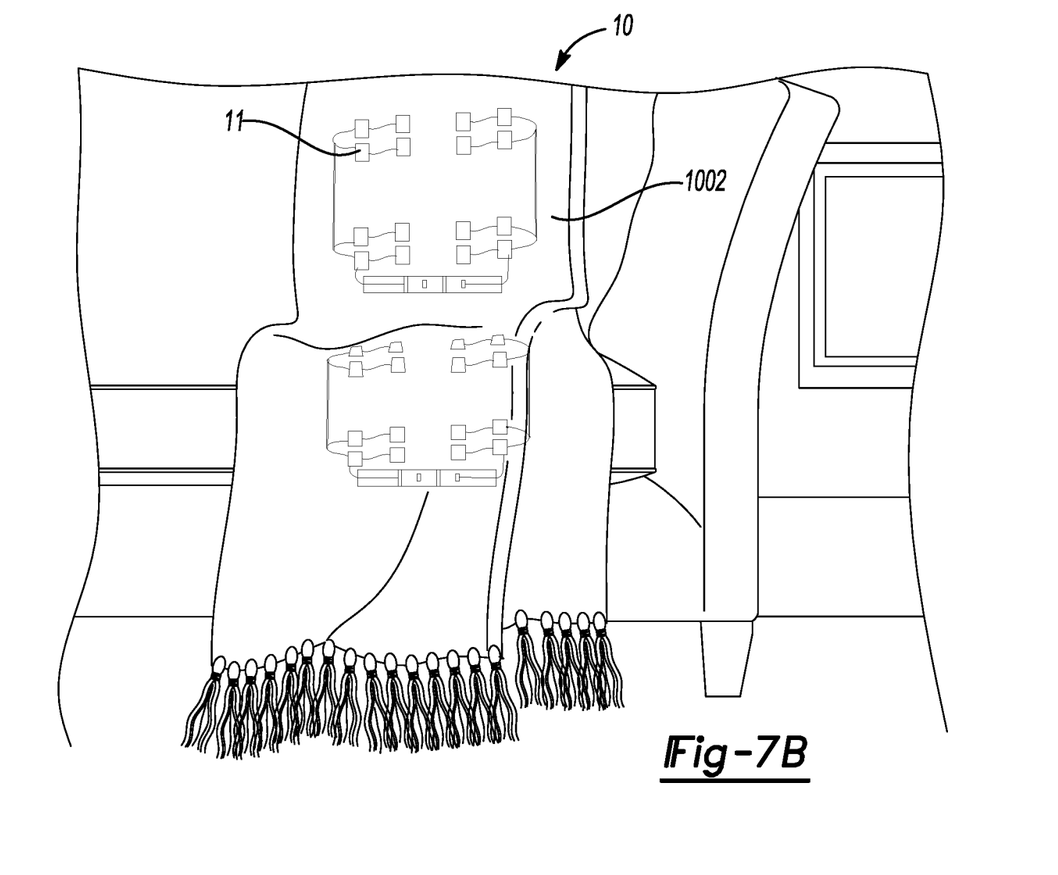
FIG. 7B illustrate the heating and/or cooling device according to the principles of the present teachings incorporated in a woven blanket.

The interconnections of each individual heating and/or cooling modules 11 (which collectively can define an array or mesh network 1000) are realized using a mesh network of series and parallel electrical circuits, as illustrated in FIG. 3. The mesh network ensures that even if one or more connections (e.g. wiring 54) of the device 10 fails, the device 10 will still maintain its functionality, as long as it is still connected to the power source 50. In some embodiments, the mesh network 1000 is knitted into wearable garments using machines, such as STOLL Model CMS 822 HP Multi-gauge E7.2. Various wearable garment concepts that integrate this invention will be referenced further below. However, it should be understood that the principles of the present teachings can be incorporated into any one of a number of materials 1002, such as fabrics, garments, woven materials, leathers, plastic, neoprene, synthetic material, natural material, and the like. In some embodiments, the material 1002 can comprise a conductive coating or treatment to facilitate thermal transmission, such as conducting polymer poly (3,4-ethylenedioxythiophene) and/or metal-free textile electrodes that are highly conductive, robust, and are low-power consuming heating elements. In some embodiments, material 1002 can plain-woven pineapple fiber textiles and cotton textiles and/or cotton yarns coated at 500 mTorr. These textiles remain light in weight and porous after coating as well. Unlike electrical heaters with conductive elements, there is no risk of experiencing electric shocks.

With continued reference to FIG. 3, power source 50 is provided for wearable heating and/or cooling device 10 and/or mesh network 1000 and provides current or voltage to provide power energy to each individual heating and/or cooling module 11 via wiring 54. In some embodiments, power source 50 can comprise batteries of various kinds suitable for a wearable device—printed, solid-state, micro, thin-film Lithium, Lithium-polymer, Lithium-ion, thin flexible supercapacitors, laminar fuel cells, stretchable, cable-shaped, transparent, or foldable—and also wall outlet, power packs, and car batteries.

A constant current regulator or other temperature controller 52 is operably connected between power source 50 and the heating and/or cooling modules 11. In some embodiments, the regulator 52 ensures that the absolute cooling or warming temperature of the wearable device 10, 1000 can be set and maintained. In some embodiments, the rate of cooling or warming of the wearable device 10, 1000 can be set and maintained.

The wearable device 10, 1000 disclosed herein can cool and/or warm the human body's temperature in any one of a number of ways, as illustrated in FIGS. 4A-7B. For example, it can be a comfort device that aids the body's natural cooling or warming function during indoor or outdoor activity, such as competitive sports, sports training, construction, military, firefighting, walking, hiking, or waiting. The wearable device 10, 1000 can further be a catastrophic incident prevention device (e.g., heat stroke, frost bite, or hypothermia) that keeps the body's core temperature within the health safety zone. It can also be an injury recovery device that aids the body's natural healing capabilities by providing cooling or warmth to the affected areas. It can be a comfort device that aids the body's natural cooling or warming function during travel (e.g. seats in car, bus, plane, train, or bike), or entertainment (e.g., seats in movie, or music venues). Moreover, it can be a comfort device that aids the body's natural cooling or warming function during rest and sleep (e.g., blanket, sleeping bag, comforter, pillow, or mattress)

It should be noted that the principles of the present teachings do not specifically require the device 10, 1000 to be worn. In fact, the invention can find utility in a wide range of applications that permit use through contact with the human body, such as by being sat on or slept on/under. Even in such applications, the device 10 is still integrated into the seat skin or sleep/rest accessory using the same CNC Knitting Machines.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A heating and/or cooling device for contact with a human body, the heating and/or cooling device comprising:
   a power source outputting electrical energy;
   a temperature controller operably coupled to the power source configured to maintain a predetermined temperature parameter by outputting regulated electrical energy; and
   at least one heating and/or cooling module operably coupled to the temperature controller for selectively receiving the regulated electrical energy and being responsive thereto to heat and/or cool the human body, the at least one heating and/or cooling module having:
      a pair of electrodes spaced apart by a filling, the filling is made of a powdered thermoelectric material comprising synthesized nano structures that remains thermoelectrically conductive to conduct the regulated electrical energy between the pair of electrodes; and
      an insulator electrically isolating the pair of electrodes, the insulator surrounding the filling and configured to provide environmental physical protection of the filling while remaining thermally conductive and electrically insulative.

2. The heating and/or cooling device according to claim 1 wherein the thermoelectric powder is selected from the group consisting of Silicon-Germanium (SiGe), Lead Telluride (PbTe), Bismuth Telluride (Bi2Te3), Silver Antimony Telluride (AgSbTe2), Germanium Telluride (GeTe), Skutterudites (CoSb3), and Zinc Antimony (Zn4Sb3).

3. The heating and/or cooling device according to claim 1 wherein the at least one heating and/or cooling module is generally cylindrical shaped having a first of the pair of electrodes positioned on a first cylindrical portion of the module and a second of the pair of electrodes positioned on a second cylindrical port of the module, the first cylindrical portion being opposingly positioned relative to the second cylindrical portion.

4. The heating and/or cooling device according to claim 1 wherein the at least one heating and/or cooling module is generally planar having a first of the pair of electrodes positioned on a first planar side of the module and a second of the pair of electrodes positioned on a second planar side of the module, the first planar side being opposingly positioned relative to the second planar side.

5. The heating and/or cooling device according to claim 1 wherein the electrodes are made from at least one of copper, graphite, titanium, brass, silver, and platinum.

6. The heating and/or cooling device according to claim 1 wherein the insulator is made from at least one of fabric, foam, glass, plastic, rubber, and wood.

7. The heating and/or cooling device according to claim 1 wherein the at least one heating and/or cooling module is coupled with a garment to be worn.

8. The heating and/or cooling device according to claim 1 wherein the at least one heating and/or cooling module is coupled with at least one of a couch, seat, and blanket.

9. The heating and/or cooling device according to claim 1 wherein the at least one heating and/or cooling module comprises a plurality of heating and/or cooling modules, the plurality of heating and/or cooling modules being coupled in series.

10. The heating and/or cooling device according to claim 1 wherein the at least one heating and/or cooling module comprises a plurality of heating and/or cooling modules, the plurality of heating and/or cooling modules being coupled in parallel.

11. The heating and/or cooling device according to claim 1 wherein the at least one heating and/or cooling module comprises a plurality of heating and/or cooling modules, the plurality of heating and/or cooling modules being coupled in an array such that failure of one of the plurality of modules does not result in failure of the array.

12. The heating and/or cooling device according to claim 1 wherein the at least one heating and/or cooling module is configured to be knitted into wearable garments using machines.

13. The heating and/or cooling device according to claim 1 wherein the at least one heating and/or cooling module is incorporated into at least one of the group consisting of fabrics, garments, woven materials, leathers, plastic, neoprene, synthetic material, and natural material.

14. The heating and/or cooling device according to claim 1 wherein the at least one heating and/or cooling module is incorporated into a material having a conductive coating or treatment configured to facilitate thermal transmission.

15. The heating and/or cooling device according to claim 1 wherein the conductive coating or treatment comprises conducting polymer poly (3,4-ethylenedioxythiophene).

16. The heating and/or cooling device according to claim 1 wherein the pair of electrodes comprises metal-free textile electrodes.

* * * * *

UNITED STATES PATENT AND TRADEMARK OFFICE
CERTIFICATE OF CORRECTION

PATENT NO. : 11,890,223 B2
APPLICATION NO. : 16/604033
DATED : February 6, 2024
INVENTOR(S) : Sridhar Lakshmanan et al.

It is certified that error appears in the above-identified patent and that said Letters Patent is hereby corrected as shown below:

In the Claims

At Column 6, Claim number 2, Line number 55, delete "(Bi2Te3)," and insert --$(Bi_2Te_3)$,--.

At Column 6, Claim number 2, Line number 56, delete "(AgSbTe2)," and insert --$(AgSbTe_2)$,--.

At Column 6, Claim number 2, Line number 57, delete "(CoSb3)," and insert --$(CoSb_3)$,--.

At Column 6, Claim number 2, Line number 57, delete "(Zn4Sb3)," and insert --$(Zn_4Sb_3)$,--.

Signed and Sealed this
Sixteenth Day of July, 2024

Katherine Kelly Vidal
*Director of the United States Patent and Trademark Office*